United States Patent [19]

Murata et al.

[11] Patent Number: 5,068,354

[45] Date of Patent: Nov. 26, 1991

[54] EPOXYSUCCINIC ACID DERIVATIVES

[75] Inventors: Mitsuo Murata, Konosu; Chihiro Yokoo, Gyoda; Kazunori Hanada, Ageo, all of Japan

[73] Assignee: Taisho Pharmaceutical Co., Ltd., Japan

[21] Appl. No.: 517,687

[22] Filed: May 2, 1990

[30] Foreign Application Priority Data

May 18, 1989 [JP] Japan .................................. 1-124753

[51] Int. Cl.$^5$ .......................................... C07D 405/12
[52] U.S. Cl. ...................................................... 548/517
[58] Field of Search ........................................ 548/517

[56] References Cited

U.S. PATENT DOCUMENTS 4,333,879 6/1982 Tamai et al. .................... 546/207

FOREIGN PATENT DOCUMENTS 2450256 9/1980 France .

OTHER PUBLICATIONS

Chemical Abstracts, vol. 94, No. 13, 30 Mar. 1981, p. 326, 98626x.
Chemical Abstracts, vol. 96, No. 5, 1 Feb. 1982, p. 254, 30617f.
Chemical Abstracts, vol. 96, No. 23, 7 Jun. 1982, p. 313, 195703u.

Primary Examiner—C. Warren Ivy
Assistant Examiner—Celia Chang
Attorney, Agent, or Firm—Lorusso & Loud

[57] ABSTRACT

An epoxysuccinic acid derivative represented by the formula

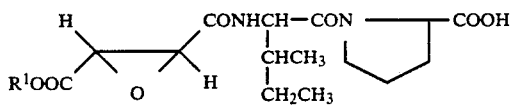

wherein $R^1$ is a hydrogen atom or an alkyl group containing 1 to 4 carbon atoms, and a pharmaceutically acceptable salt are useful as cathepsin B inhibitors.

5 Claims, No Drawings

EPOXYSUCCINIC ACID DERIVATIVES

BACKGROUND OF THE INVENTION

1. Field of the Invention

The present invention relates to epoxysuccinic acid derivatives, and more particularly to epoxysuccinic acid derivatives inhibiting cathepsin B specifically with low toxicity, and the synthesis intermediates thereof.

Statement of the Prior Art

Calcium-activated neutral protease (CANP), cathepsin B and cathepsin L, which belong to thiol proteases, are considered to be associated with the decomposition of the muscular structure protein in malignant muscular atrophy deseases such as muscular dystrophy and distal myophathy.

N-(L-3-trans-carboxyoxirane-2-carbonyl)-L-leucylagmatine [Agric. Biol. Chem., vol. 42, pp. 523-528 (1978)], epoxysuccinyl dipeptide derivatives (U.K. Patent No. 2,046,730) and the like have been heretofore known as the compounds inhibiting several thiol proteases. However, no epoxysuccinic acid derivatives inhibiting specifically only one of the thiol proteases have been known.

As a result of the earnest research to the compounds having an epoxy ring, the present inventors have found that the compounds prepared from the compounds which are included within the structural formula in U.K. patent No. 2,046,730 but are not specifically described in the patent specification, inhibit cathepsin B specifically unlike the known compounds, and have accomplished the present invention.

SUMMARY OF THE INVENTION

An object of the present invention is to provide an epoxysuccinic acid derivative represented by the formula

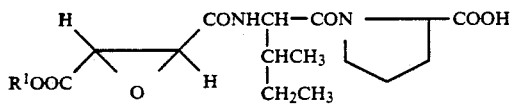

wherein $R^1$ is a hydrogen atom or an alkyl group containing 1 to 4 carbon atoms, and a pharmaceutically acceptable salt.

Another object of the present invention is to provide the synthetic intermediates of the compound of Formula I. This intermediate is an epoxysuccinic acid derivatives represented by the formula

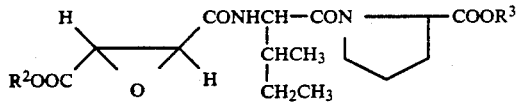

wherein $R^2$ and $R^3$ are the same or different, and are each an alkyl group containing 1 to 4 carbon atoms or a protecting group of the carboxyl group.

DETAILED DESCRIPTION OF THE INVENTION

In the present invention, the alkyl group having 1 to 4 carbon atoms refers to a straight chain alkyl group such as, for example, a methyl group, an ethyl group, a propyl group and a butyl group. The protecting group of the carboxyl group refers to those used usually in the field of the peptide synthesis chemistry, for example, a benzyl group, a p-methoxybenzyl group, a p-nitrobenzyl group, a t-butyl group and a benzhydryl group.

The pharmaceutically acceptable salts of the present invention are salts with inorganic bases including sodium, potassium, magnesium, ammonium and the like, salts with organic bases (e.g., triethylamine and cyclohexylamine), salts with basic amino acids (e.g., arginine and lysine), salts with mineral acids (e.g., sulfuric acid, hydrochloric acid and phosphoric acid), salts with organic acids (e.g., acetic acid, lactic acid, tartaric acid, fumaric acid and maleic acid) and salts with acidic amino acids (e.g., glutamic acid and aspartic acid).

Preferred compounds of Formula I are N-(L-3-trans-ethoxycarbonyloxirane-2-carbonyl)-L-isoleucyl-L-proline, N-(L-3-trans-carboxyoxirane-2-carbonyl)-L-isoleucyl-L-proline, N-(L-3-trans-ethoxycarbonyloxirane-2-carbonyl)-L-isoleucyl-L-proline sodium salt and N-(L-3-trans-methoxycarbonyloxirane-2-carbonyl)-L-isoleucyl-L-proline.

The compounds of Formula I may be prepared, for example, by the following process.

The compound of the following formula

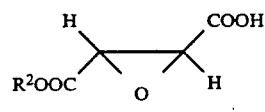

wherein $R^2$ is as defined above, is condensed with a compound of the following formula

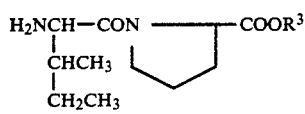

wherein $R^3$ is as defined above, in a solvent (e.g., chloroform, ethyl acetate and N,N-dimethylformamide) according to a method used usually in the field of the peptide synthesis chemistry such as an N,N-dicyclohexylcarbodiimide method, a mixed anhydride method and an activated ester method to give the compound of Formula II.

The compound of Formula II of the present invention may be subjected to removal of the alkyl group and/or the protecting group of the carboxyl group according to a method used usually in the field of the peptide synthesis chemistry to give the compound of Formula I of the present invention. Examples of such method are catalytic reduction and catalytic transfer hydrogenation (CTH) in a solvent such as methanol, ethanol and N,N-dimethylformamide with a catalyst such as palladium carbon and palladium black, a method using acids (e.g., trifluoroacetic acid, methanesulfonic acid, hydrobromic acid and hydrochloric acid) and hydrolysis. The alkyl group for $R^1$ in Formula I are the same as the alkyl group having 1 to 4 carbon atoms for $R^2$ in Formula II.

The compounds of Formula III can be prepared according to the method described in Chem. Pharm. Bull., vol. 35, pp. 1098-1104 (1987). The compound of Formula IV also can be prepared from isoleucine and proline according to a method used usually in the field of the peptide synthesis chemistry.

The compounds of Formula I thus obtained hardly inhibit CANP and papain which also belongs to thiol proteases but strongly inhibit cathepsin B specifically. For the use of the compounds of Formula I for treatment of the muscular atrophy deseases, these compounds are administered orally or parenterally in the forms of tablets, pills, capsules, granules and injectional preparations. These preparations can be prepared according to the conventional practices using ordinary additives such as fillers, binders, disintegrators, pH-adjusting agents and solubilizers.

The dosage of the compound of Formula I for therapy to a patient depends on the age of the patient and kind and conditions of the diseases, but usually it is in the range from 10 to 20000 mg in single or several divided doses per day.

Test examples are shown as follows.

Test example 1 [Inhibitory Activity against CANP]

The activity was measured according to the method of S. Ishiura et al [J. Biochem., vol. 84, page 225 (1978)].

Each of 0.45 ml of the reaction solutions containing 25 mM 2-mercaptoethanol, 5 mM calcium chloride, 0.1 M sodium glycerophosphate-HCl (pH 7.5), 0.24% alkali-denatured casein, 1% dimethyl sulfoxide and various concentrations of the test drug was preincubated at 30° C. for 5 minutes, and 5 μg of μCANP (50 μg) (Calpain I, Nacalai Tesque Inc.) was added or starting the reaction. After incubation at 30° C. for 20 minutes, the reaction was stopped by addition of 0.5 ml of 10% trichloroacetic acid. After allowing to stand at room temperature for 60 minutes, the mixture was centrifuged at 3000×g for 5 minutes, and the absorbance at 280 nm of the supernatant was determined. The remaining activity was obtained by reducing the blank value which was obtained in a similar manner to the above but adding 10% trichloroacetic acid prior to addition of μCANP from the above value. The concentration of the test drug required for 50% inhibition ($IC_{50}$) was calculated from the inhibition rate obtained using the value which was measured in a similar manner to the above but without the test drug. The $IC_{50}$ value of the compound obtained in Example 5 was more than 200,000 nM.

Test example 2 [Inhibitory Activity against Papain]

The activity was measured according to the method of A.J. Barrett et al [Biochem. J., vol. 201, page 189, (1982)].

To each of 0.95 ml of the reaction solutions containing 2.5 mM 2-mercaptoethanol, 1 mM disodium ethylenediaminetetraacetate, 0.1 M sodium potassium phosphate (pH 6.8), 0.1% brij-35 (Nacalai Tesque Inc.), 1% dimethyl sulfoxide and the various concentrations of the test drug was added 25 μl of 400 nM papain solution (Sigma Chemical Co.), and the mixture was preincubated for 40° C. for 3 minutes, after which 25 μof 200 μM benzyloxycarbonyl-L-phenylaranyl-L-arginine 4-methyl-coumaryl-7-amide (Peptide Institute Inc.) was added for starting the reaction. After incubation at 40° C. for 10 minutes, the reaction was stopped by addition of 1 ml of 100 mM sodium chloroacetate in 100 mM sodium acetate (pH 4.3). The fluorescence of the liberated 7-amino-4-methylcoumarine was determined using a Shimazu fluorimeter RF-5000 with excitation at 380 nm and emission measured at 440 nm. The concentration of the test drug required for 50% inhibition ($IC_{50}$) was calculated from the inhibiting rate calculated using the value which was measured in a similar manner to the above but without the test drug. The $IC_{50}$ value of the compound obtained in Example 5 was 16000 nM.

Test example 3 [Inhibitory Activity against Cathepsin B]

The activity was measured according to the method of A.J. Barrett et al [Biochem. J., vol. 201, page 189, (1982)].

To each of 0.95 ml of the reaction solutions containing 2.5 mM 2-mercaptoethanol, 1 mM disodium ethylenediaminetetraacetate, 0.1 M sodium potassium phosphate buffer (pH 6.0), 0.1% brij-35 (Nacalai Tesque Inc.), 1% dimethyl sulfoxide and different concentrations of the test drug was added 25 μl of 200 nM cathepsin B solution (Sigma Chemical Co.), and the mixture was preincubated for 40° C. for 10 minutes, after which 25 μl of 200 M benzyloxycarbonyl L-phenylaranyl-L-arginine 4-methylcoumaryl-7-amide (Peptide Institute Inc.) was added for starting the reaction. After incubation at 40° C. for 10 minutes, the reaction was stopped by addition of 1 ml of 100 mM sodium chloroacetate in 100 mM sodium acetate (pH 4.3) The fluorescence of the liberated 7-amino-4-methylcoumarine was determined using a Shimazu fluorimeter RP-5000 with excitation at 380 n and emission measured at 440 nm. The concentration of the test drug required for 50% inhibition ($IC_{50}$) was calculated from the inhibiting rate calculated using the value which was measured in a similar manner to the above but without the test drug. Chosen as a comparative drug is N-(L-3-trans-carboxy-oxirane-2-carbonyl)-L-isoleucyl-L-proline methyl ester which is included within the structural formula of the above U.K. Patent and is the closest compound to the compound of formula I in the structure. Results are shown in Table 1.

TABLE 1

| Inhibitory activity value [$IC_{50}$ (nM)] | |
|---|---|
| Drug | Cathepsin B |
| A | 120 |
| B | 8800 |

Note
A: The compound obtained in Example 5
B: N-(L-3-trans-carboxyoxirane-2-carbonyl)-L-isoleucyl-L-proline methyl ester (Reference Example)

It is apparent from the above test examples that the compound of formula I have the strong and specific inhibitory activity against cathepsin B.

The present invention is illustrated in more detail by the following Examples.

EXAMPLE 1

Preparation of N-(L-3-trans-ethoxycarbonyl-oxirane-2-carbonyl)-L-isoleucyl-L-proline benzyl ester In 5 ml of 4 N hydrochloric acid in dioxane was dissolved 437 mg (1.0 mmole) of N-t-butoxycarbonyl-L-isoleucyl-L-proline benzyl ester, and the solution was stirred at room temperature for an hour. The reaction solution was evaporated to dryness under reduced pressure, and the residue was dissolved in 4 ml of chloroform, and 323 mg (1.23 mmole) of L-trans-epoxysuccinic acid ethyl p-nitrophenyl ester was added thereto. A solution of 116 mg (1.2 mmole) of triethylamine in 1 ml of chloroform was added under ice-cooling with stirring, and the mixture was stirred under ice-cooling for 2 hours and then at room temperature overnight. To the reaction solution was added 100 ml of ethyl acetate, and the mixture was washed twice with 100 ml of brine.

The organic layer was dried over anhydrous magnesium sulfate, filtered and concentrated under reduced pressure. The residue was purified by column chromatography on silica gel (Eluent; ethyl acetate : n-hexane =1:1) to give 387 mg of the title compound.

IR $v_{max}^{neat}$ cm$^{-1}$; 3273, 2966, 1746, 1693, 1629, 1542, 1455, 1277, 1200, 1171, 1026 NMR (CDCl$_3$)δ(ppm); 0.85 (3H, t, J=7Hz), 0.95-1.18 (1H, m), 0.97 (3H, d, J=7Hz), 1.32 (3H, t, J=7Hz), 1.35-1.60 (1H, m), 1.70-2.40 (5H, m), 3.47 (1H, d, J=2Hz), 3.60-3.90 (2H, m), 3.65 (1H, d, J=2Hz), 4.26 (2H, dq, J=2,7Hz), 4.50-4.70 (2H, m), 5.13 (1H, d, J=12Hz), 5.20 (1H, d, J=12Hz), 6.72 (1H, d, J=9Hz), 7.35 (5H, s)

MS (EI); m/e: 460 (M+)

EXAMPLE 2

Preparation of N-(L-3-trans-benzyloxycarbonyl-oxirane-2-carbonyl)-L-isoleucyl-L-proline methyl ester In a similar manner to that of Example 1, 2.00 g (5.8 mmole) of N-t-butoxycarbonyl-L-isoleucyl L-proline methyl ester was treated with 10 ml of 4 N hydrochloric acid in dioxane for removal of the t-butoxycarbonyl group, and then the resulting product was condensed with 2.19 g (6.4 mmole) of L-trans epoxysuccinic acid benzyl p-nitrophenyl ester in the presence of 650 mg (6.4 mmole) of triethylamine in 12 ml of chloroform. After a similar work-up to that of Example 1, purification by column chromatography on silica gel (Eluent; ethyl acetate : n-hexane=1:1) gave 2.39 g of the title compound.

IR $v_{max}^{neat}$ cm$^{-1}$; 3276, 2965, 1747, 1693, 1627, 1541, 1451, 1280, 1246, 1195, 897

NMR (CDCl$_3$)δ(ppm); 0.90 (3H, t, J=7Hz), 0.95-1.17 (1H, m), 0.98 (3H, d, J=7Hz), 1.39-1.60 (1H, m), 1.75-2.36 (5H, m), 3.52 (1H, d, J=2Hz), 3.57-3.90 (2H, m), 3.69 (1H, d, J=2Hz), 3.72 (3H, s), 4.45-4.55 (1H, m), 4.61 (1H, dd, J=8,9Hz), 5.17 (1H, d, J=12Hz), 5.27 (1H, d, J=12Hz), 6.74 (1H, d, J=9HZ), 7.38 (5H, s)

MS (EI); m/e: 446 (M+)

EXAMPLE 3

Preparation of N-(L-3-trans-benzyloxycarbonyl-oxirane-2-carbonyl)-L-isoleucyl-L-proline benzyl ester In a similar manner to that of Example 1, 427 mg (1.0 mmole) of N-t-butoxycarbonyl-L-isoleucyl-L-proline benzyl ester was treated with 5 ml of 4 N hydrochloric acid in dioxane for removal of the t-butoxycarbonyl group, and then the resulting product was condensed with 385 mg (1.1 mmole) of L-trans-epoxysuccinic acid benzyl p-nitrophenyl ester in the presence of 114 mg (1.1 mmole) of triethylamine in 5 ml of chloroform. After a similar work-up to that of Example 1, purification by column chromatography on silica gel (Eluent; ethyl acetate : n-hexane=2:3) gave 393 mg of the title compound.

IR $v_{max}^{neat}$ cm$^{-1}$; 3725, 2965, 1733, 1688, 1652, 1541, 1456, 1384, 1348, 1168, 1102, 897

NMR (CDCl$_3$) δ(ppm); 0.85 (3H, t, J=7Hz), 0.95 (3H, d, J=7Hz), 0.95-1.15 (1H, m), 1.33-1.58 (1H, m), 1.70-2.35 (5H, m), 3.51 (1H, d, J=2Hz), 3.58-3.88 (2H, m), 3.68 (1H, d, J=2Hz), 4.50-4.65 (2H, m), 5.13 (1H, d, J=12Hz), 5.15 (1H, d, J=12Hz), 5.20 (1H, d, J=12Hz), 5.27 (1H, d, J=12Hz), 6.71 (1H, d, J=9Hz), 7.35 (5H, s), 7.39 (5H, s)

MS (EI); m/e: 522 (M+)

EXAMPLE 4

Preparation of N-(L-3-trans-methoxycarbonyl-oxirane-2-carbonyl)-L-isoleucyl-L-proline benzyl ester In a similar manner to that of Example 1, 1.41 g (3.4 mmole) of N-t-butoxycarbonyl-L-isoleucyl-L-proline benzyl ester was treated with 10 ml of 4 N hydrochloric acid in dioxane for removal of the t-butoxycarbonyl group, and then the resulting compound was condensed with 990 mg (3.7 mmole) of L-transepoxysuccinic acid methyl p-nitrophenyl ester in the presence of 375 mg (3.7 mmole) of triethylamine in 30 ml of chloroform. After a similar work-up to that of Example 1, purification by column chromatography on silica gel (Eluent; ethyl acetate : n-hexane=1:1) gave 1.25 g of the title compound.

IR $v_{max}^{KBr}$ cm$^{-1}$; 3274, 2964, 1747, 1693, 1627, 1542, 1446, 1352, 1210, 1173, 1003, 895

NMR (DMSO-d$_6$) δ(ppm); 0.79 (3H, t, J=7Hz), 0.85 (3H, d, J=7Hz), 0.92-1.25 (1H, m), 1.35-1.60 (1H, m), 1.65-2.30 (5H, m), 3.50-3.85 (2H, m), 3.63 (1H, d, J=2Hz), 3.71 (3H, s), 3.77 (1H, d, J=2Hz), 4.33-4.50 (2H, m), 5.12 (2H, s), 7.36 (5H, s), 8.78 (1H, d, J=8Hz), MS (FAB); m/e: 447 (MH+)

EXAMPLE 5

Preparation of N-(L-3-trans-ethoxycarbonyl-oxirane-2-carbonyl)-L-isoleucyl-L-proline In 5 ml of ethanol was suspended 15 mg of 10% palladium carbon, and a solution of 467 mg (1.0 mmole) of the compound, obtained in Example 1, in 5 ml of ethanol was added. The mixture was stirred at room temperature under hydrogen, and the catalyst was removed by filtration and washed with ethanol. The filtrate and the washings were combined and evaporated under reduced pressure to give 324 mg of the title compound.

IR $v_{max}^{KBr}$ cm$^{-1}$; 3276, 2970, 1747, 1682, 1627, 1546, 1452, 1201, 1026, 899

NMR (DMSO-d$_6$) δ(ppm); 0.84 (3H, t, J=7Hz), 0.93 (3H, d, J=7Hz), 0.95-1.25 (1H, m), 1.23 (3H, t, J=7Hz), 1.38-1.62 (1H, m), 1.65-2.30 (5H, m), 3.49-385 (2H, m), 3.60 (1H, d, J=2Hz), 3.77 (1H, d, J=2H), 4.19 (2H, q, J=7Hz), 4.19-4.30 (1H, m), 4.43 (1H, dd, J=9,9Hz), 8.79 (1H, d, J=9Hz), 12.30-12.80 (1H, br)

EXAMPLE 6

Preparation of N-(L-3-trans-caboxyoxirane-2-carbonyl)-L-isoleucyl-L-proline

In a similar manner to that of Example 5, 697 mg (1.3 mmole) of the compound obtained in Example 3 was hydrogenated over 70 mg of 10% palladium carbon in 12 ml of methanol. The resulting crude product was chromatographed on Lobar prepacked column Lichroprep RP-18 (Merck Co., Eluent; 0.1% aqueous trifluoroacetic acid solution : acetonitril =75:25) and then on a column packed with Sephadex G-10 (Pharmacia Fine Chemicals, Eluent: water) to give the fractions containing the title compound, which were then lyophilized to give 244 mg of the title compound.

IR $v_{mzx}^{KBr}$cm$^{-1}$; 3421, 2970, 1734, 1624, 1551, 1456, 1192, 897

NMR (DMSO-d$_6$) δ(ppm); 0.84 (3H, t, J=7Hz), 0.92 (3H, d, J=7Hz), 0.95-1.27 (1H, m), 1.35-1.62 (1H, m), 1.65-2.30 (5H, m), 3.47 (1H, d, J=2Hz), 3.50-3.85 (2H, m), 3.71 (1H, d, J=2Hz), 4.20-4.31 (1H, m), 4.44 [1H, dd, J=9,9Hz), 874 (1H, d, J=9Hz), 11.30-14.00 (2H, br)

MS (FAB); m/e: 343 (MH+)

EXAMPLE 7

Preparation of N-(L-3-trans-ethoxycarbonyl-oxirane-2-carbonyl)-L-isoleucyl-L-proline sodium salt To a solution of 450 mg (1.2 mmole) of the compound, obtained in Example 5, in a small amount of ethanol was added a solution of 112 mg (1.3 mmole) of sodium hydrogen carbonate in 2 ml of water. Then the solution obtained was chromatographed on a column packed with Sephadex G-10 (Pharmacia Fine Chemicals, Eluent; Water:) to give the fractions containing the title compound, which were then lyophilized to give 370 mg of the title compound.

IR $\nu_{mzx}^{KBr}$cm$^{-1}$; 3436, 2970, 1751, 1688, 1626, 1544, 1453, 1397, 1203, 1027, 900

NMR (DMSO-d$_6$) δ(ppm); 0.75–1.1.8 (7H, m), 1.23, 1.24 (3H, t, J=7Hz), 1.30–1.60 (1H, m), 3.50–3.85 (1H, m), 3.60, 3.73 (1H, d, J=2Hz), 3.77, 3.88 (1H, d, J=2Hz), 4.00–4.25 (3H, m), 4.35–4.55 (1H, m), 8.41, 8.71 (1H, d, J=9Hz)

MS (FAB); m/e: 393 (MH+)

EXAMPLE 8

Preparation of N-(L-3-trans-methoxycarbonyl-oxirane-2-carbonyl)-L-isoleucyl-L-proline In a similar manner to that of Example 5, 930 mg (2.1 mmole) of the compound obtained in Example 4 was hydrogenated over 10 mg of 10% palladium carbon in 20 ml of methanol. The catalyst was removed by filtration and washed with methanol. The filtrate and washing were combined and evaporated under reduced pressure to give 690 mg of the title compound.

IR $\nu_{mzx}^{KBr}$m$^{-1}$; 3277, 2967, 1752, 1681, 1627, 1547, 1449, 1212, 896

NMR (DMSO-d$_6$) δ(ppm); 0.83 (3H, t, J=7Hz), 0.92 (3H, d, J=7Hz), 0.95–1.28 (1H, m), 1.36–1.64 (1H, m), 1.65–2.28 (5H, m), 3.50–3.85 (2H, m), 3.64 (1H, d, J=2Hz), 3.72 (3H, s), 3.77 (1H, d, J=2Hz), 4.19–4.30 (1H, m), 4.44 (1H, dd, J=9,9Hz), 8.76 (1H, d, J=9Hz), 12.30–12.70 (2H, br)

MS (FAB); m/e: 357 (MH+)

REFERENCE EXAMPLE

Preparation of N-(L-3-trans-carboxyoxirane-2-carbonyl)-L-isoleucyl-L-proline methyl ester In a similar manner to that of Example 5, 1.50 g (3.4 mmole) of the compound obtained in Example 2 was hydrogenated over 30 mg of 10% palladium carbon in 12 ml of methanol. The resulting crude product was chromatographed on Lobar prepacked column Lichroprep RP-18 (Merck Co., Eluent; water : acetonitril=7:3) to give the fractions containing the title compound, which were then evaporated under reduced pressure to give 835 mg of the title compound.

IR $\nu_{max}^{KBr}$cm$^{-1}$ 3284, 2966, 1747, 1682, 1626, 1546, 1451, 1280, 1198, 1178, 897

NMR (DMSO-d$_6$) δ(ppm); 0.83 (3H, t, J=7Hz), 0.92 (3H, d, J=7Hz), 0.95–1.25 (1H, m), 1.35–1.61 (1H, m), 1.65–2.30 (5H, m), 3.45 (1H, d, J=2Hz), 3.50–3.85 (2H, m), 3.60 (3H, s), 3.70 (1H, d, J=2Hz), 4.26–4.38 (1H, m), 4.43 (1H, dd, J=9,9Hz), 8.73 (1H, d, J=9Hz)

MS (FAB); m/e: 367 (MH+)

What is claimed is:

1. An epoxysuccinic acid derivative represented by the formula

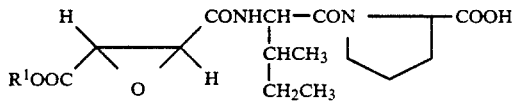

wherein R$^1$ is a hydrogen atom or an alkyl group containing 1 to 4 carbon atoms, and a pharmaceutically acceptable salt.

2. N-(L-3-trans-ethoxycarbonyloxirane-2-carbonyl)-L-isoleucyl-L-proline.

3. N-(L-3-trans-carboxyoxirane-2-carbonyl)-L-isoleucyl-L-proline.

4. N-(L-3-trans-ethoxycarbonyloxirane-2-carbonyl)-L-isoleucyl-L-proline sodium salt.

5. N-(L-3-trans-methoxycarbonyloxirane-2-carbonyl)-L-isoleucyl-L-proline.

* * * * *

UNITED STATES PATENT AND TRADEMARK OFFICE
CERTIFICATE OF CORRECTION

PATENT NO. : 5,068,354
DATED : November 26, 1991
INVENTOR(S) : MURATA et al

It is certified that error appears in the above-identified patent and that said Letters Patent is hereby corrected as shown below:

Col. 3, line 25, "(50 µg)" should read --(50 µl)--;

line 26, "or" should read --for--; and line 54, "µof" should read --µl of--.

Col. 4, line 23, "n" should read --nm--.

Col. 5, line 34, "(CDCl $_3$)-- should read --(CDCl$_3$)--.

Col. 6, line 42, "3.49-385" should read --3.49-3.85--;

line 43, "(1H, d, J=2H)" should read --(1H, d, J=2Hz)--;

between lines 45 and 46, insert the following sentence --MS(FAB); m/e: 371(MH+)--.

line 61, "$_{mzx}$" should read --$_{max}$--;

line 67, "874" should read --8.74--.

UNITED STATES PATENT AND TRADEMARK OFFICE
CERTIFICATE OF CORRECTION

PATENT NO. : 5,068,354

DATED : November 26, 1991

INVENTOR(S) : MURATA et al

It is certified that error appears in the above-identified patent and that said Letters Patent is hereby corrected as shown below:

Col. 7, line 14, "$_{mzx}$" should read --$_{max}$--.

line 34 "$_{mzx}$" should read --$_{max}$--.

Col. 8, line 14, "cm-1" should read --$cm^{-1}$--.

Signed and Sealed this

Thirteenth Day of April, 1993

Attest:

STEPHEN G. KUNIN

Attesting Officer

Acting Commissioner of Patents and Trademarks